United States Patent
Sasov et al.

(10) Patent No.: US 9,649,076 B2
(45) Date of Patent: May 16, 2017

(54) X-RAY CT APPARATUS WITH A FILTERING ELEMENT EXHIBITING A MAXIMUM ABSORPTION AT ITS CENTER

(71) Applicant: Bruker microCT NV, Kontich (BE)

(72) Inventors: Alexander Sasov, Puurs (BE); Jeroen Hostens, Gentbrugge (BE)

(73) Assignee: Bruker microCT NV, Kontich (BE)

( * ) Notice: Subject to any disclaimer, the term of this patent is extended or adjusted under 35 U.S.C. 154(b) by 75 days.

(21) Appl. No.: 14/850,979

(22) Filed: Sep. 11, 2015

(65) Prior Publication Data

US 2016/0073982 A1     Mar. 17, 2016

(30) Foreign Application Priority Data

Sep. 17, 2014 (EP) .................................. 14185226

(51) Int. Cl.
| | | |
|---|---|---|
| A61B 6/03 | (2006.01) | |
| A61B 6/00 | (2006.01) | |
| G21K 1/10 | (2006.01) | |

(52) U.S. Cl.
CPC ............ *A61B 6/4035* (2013.01); *A61B 6/508* (2013.01); *G21K 1/10* (2013.01)

(58) Field of Classification Search
CPC ........... A61B 6/03; A61B 6/032; A61B 6/035; A61B 6/4035; A61B 6/508; G21K 1/10
See application file for complete search history.

(56) References Cited

U.S. PATENT DOCUMENTS

| | | | | |
|---|---|---|---|---|
| 6,108,403 A * | 8/2000 | Cooper, III | ............... | G21K 1/10 378/156 |
| 6,148,062 A * | 11/2000 | Romeas | .................... | G21K 1/10 378/156 |
| 6,968,042 B2 * | 11/2005 | Toth | ........................ | A61B 6/032 378/119 |
| 7,430,282 B2 * | 9/2008 | Mori | ...................... | A61B 6/032 378/145 |
| 7,649,973 B1 | 1/2010 | Li | | |
| 8,180,017 B2 * | 5/2012 | Forthmann | ............ | A61B 6/032 378/156 |
| 8,873,704 B2 * | 10/2014 | Stierstorfer | ............ | A61B 6/032 378/16 |
| 9,254,109 B2 * | 2/2016 | Becker | ................... | A61B 6/032 |

(Continued)

FOREIGN PATENT DOCUMENTS

| | | |
|---|---|---|
| DE | 20 2014 002 844 | 6/2014 |
| EP | 2 634 775 | 9/2013 |

(Continued)

*Primary Examiner* — Thomas R Artman
(74) *Attorney, Agent, or Firm* — Paul Vincent

(57) ABSTRACT

An X-ray computed tomography (=CT) apparatus (10) has a filter element (2) for attenuating an X-ray beam (1). The filter element (2) has a spatially varying X-ray absorption capability along a cross direction (y) which is perpendicular to both the beam axis (z) of the X-ray beam and to a rotation axis (x) of a gantry. The spatially varying X-ray absorption capability exhibits a maximum absorption along the cross direction (y) at a zero position (y0), wherein X-rays passing through the filter element (2) at the zero position (y0) intersect the rotation axis (x). The CT apparatus allows for further reduction of the radiation dose for an object to be investigated, while simultaneously retaining high image quality.

17 Claims, 2 Drawing Sheets

(56) References Cited

U.S. PATENT DOCUMENTS

| | | | |
|---|---|---|---|
| 2005/0058254 A1* | 3/2005 | Toth | A61B 6/032 378/156 |
| 2005/0094769 A1 | 5/2005 | Heismann | |
| 2008/0123816 A1 | 5/2008 | Mori | |
| 2012/0002782 A1 | 1/2012 | Yoshida | |
| 2012/0219106 A1* | 8/2012 | Stierstorfer | A61B 6/032 378/15 |

FOREIGN PATENT DOCUMENTS

| | | |
|---|---|---|
| WO | WO 2009/083848 | 7/2009 |
| WO | WO 2012/174246 | 12/2012 |
| WO | WO 2013/182928 | 12/2013 |

\* cited by examiner

X-RAY CT APPARATUS WITH A FILTERING ELEMENT EXHIBITING A MAXIMUM ABSORPTION AT ITS CENTER

This application claims Paris convention priority from EP 14 185 226.9 filed Sep. 17, 2014 the entire disclosure of which is hereby incorporated by reference.

BACKGROUND OF THE INVENTION

The invention relates to an X-ray computed tomography (=CT) apparatus, comprising
an X-ray source for emitting an X-ray beam, in particular a divergent X-ray beam, along a beam axis (z),
a filter element for attenuating the X-ray beam,
a stage for an object to be investigated with the attenuated X-ray beam,
a 2D X-ray detector with a detection area,
and a gantry system capable of rotating either the entirety of the X-ray source, the filter element and the 2D X-ray detector, or the stage for the object with respect to a rotation axis (x) which is perpendicular to the beam axis (z), wherein the filter element has a spatially varying X-ray absorption capability along a cross direction (y) which is perpendicular to both the beam axis (z) and the rotation axis (x).

Such a CT apparatus is known from US 2012/0002782 A1.

The use of X-rays in imaging is a well-established technology, in particular in medicine and science. The basic principle is that the X-rays produced by an X-ray source are partially attenuated by an object to be investigated, and that the X-rays which have enough energy to pass through the object are detected by a two dimensional (2D) X-ray detector (camera), resulting in a two-dimensional (2D) image. This image is also referred to as a projection image. Different types of X-ray sources are used in combination with different cameras, however, the basic principle remains.

In order to generate a three-dimensional (3D) image of the object, projection images have to be acquired from different angles. This can be done by rotating the object, or by rotating the X-ray source together with the camera around the object. In both cases a dataset of 2D projection images is generated. These projection images are then used to generate a new dataset of cross-sections by a process called back-projection. It is from this second cross-sectional dataset from which the 3D information can be obtained. This method is also referred to as computed tomography (CT).

A particular field of interest in preclinical research is the investigation of small living animals, such as mice or rats. When dealing with live animals, rotating the animal is often not advisable. Therefore special scanners have been developed where the animal is placed on a bed, which, just like in a clinical scanner, moves inside the scanner while both the X-ray source and the camera rotate around the bed acquiring projection images at multiple angles.

Imaging live animals using X-rays always results in a certain radiation dose; without X-rays there would not be an image. An important point to consider when scanning live animals is to reduce the radiation dose in order to minimize or even avoid any biological effects.

In the past, filters have been placed between the X-ray source and the object; the filters were designed to preferentially absorb the low energy X-rays. Typically, these filters were made of sheets of metal (e.g. aluminum) with a well-defined and uniform thickness.

Using such a filter, the low energy X-rays are predominantly attenuated by the filter and no longer by the animal, and the total radiation dose is reduced.

Increasing the thickness of the filter or changing the filter type (e.g. from aluminum to copper) will absorb more X-rays, thereby further reducing the radiation dose. However, if the X-ray intensity becomes too low, or the X-ray energy becomes too high, the image quality will deteriorate. Therefore, optimal combinations of X-ray energies and filters are looked for in order to minimize the total radiation dose while still obtaining an image with enough information allowing image analysis.

US 2012/0002782 A1 proposes a CT apparatus wherein an X-ray source and a 2D X-ray detector are rotated around a bed for a human patient. A compensation filter with a varying thickness, and therefore a varying X-ray absorption capability, is located in front of the X-ray source. The center of the compensation filter, which shadows X-rays intersecting an axis of rotation, exhibits a minimum thickness, and thus a minimum of X-ray absorption. Another CT apparatus is known from WO 2013/182928 A1, wherein a filter of basically triangular shape is introduced into an X-ray beam from the side, such that the X-ray beam is attenuated to the largest degree at its edge, and less at its center.

The latter filters, or rather beam shaping inserts or absorbers, are intended for equalizing intensity of radiation which reaches the detector array. The absorber provides a thin layer of material in the central part of the beam and thicker layers in periphery areas. The shape of such absorbers is based on the assumption that a human or animal body shows more absorption of X-ray radiation in the central area and less in the periphery. The shape of the absorbing layer applied to the primary beam is inverted to the expected local thicknesses of the scanning object, which finally equalizes the signals on the detector array across illuminated area. In this way, the required dynamic range of detectors used in tomographical and microtomographical set-ups can be reduced.

It is the object of present invention to provide a CT apparatus which allows to further reduce the radiation dose for an object to be investigated, while retaining a high image quality at the same time.

SUMMARY OF THE INVENTION

This object is achieved, in accordance with the invention, by a CT apparatus as introduced in the beginning, characterized in that the spatially varying X-ray absorption capability exhibits a maximum absorption along the cross direction (y) at a zero position (y0), wherein X-rays passing through the filter element at the zero position (y0) intersect the rotation axis (x).

The basic idea of the present invention is to deliberately reduce the X-ray intensity close to the rotation axis of the gantry system, whereas farther away from the rotation axis, the X-ray intensity is kept higher. Further, in accordance with the invention, the average X-ray energy close to the rotation axis may be increased, whereas farther away from the rotation axis, the average X-ray energy may be kept lower, and preferably nearly unchanged. This is done by means of a corresponding filter element with a spatially varying X-ray absorption capability. The filter has a maximum absorption, and may create a maximum shift to higher average X-ray energies, in the region corresponding to (i.e. shadowing) the rotation axis, i.e. at the zero position y0, typically by means of a maximum thickness there. In general, the filter element attenuates low energy X-rays to a higher degree, and preferably much higher degree, than high energy X-rays.

Reducing the X-ray intensity close to the rotation axis will reduce the signal to noise ratio in the corresponding region of the detection area of the 2D X-ray detector (typically at the center of its detection area) and the corresponding projection images, respectively, which also deteriorates the image quality of cross sections. However, when calculating cross-sections in the course of the reconstruction algorithm (by back projection, in particular filtered back projection), more information is available from the various projection images the closer you come to the rotation axis, increasing the image quality of cross-sections there. Therefore, the loss in signal to noise ratio will be compensated for by the information increase closer to the rotation axis. Preferably, the intensity reduction approximately matches the information increase such that a uniform image quality within a cross-section (from its center to its edges) is obtained.

As a result, the reduction in X-ray intensity and the increase of the average X-ray energy close to the rotation axis will decrease the overall radiation dose for the object to be investigated (such as a living human or animal body or a part thereof), in particular in a region which is often very sensitive to radiation damage (such as the bone marrow or intestines), without reducing the overall image quality of cross-sections.

Note that the elements of the CT apparatus are arranged such that an X-ray beam emitted by the X-ray source first passes through the filter element, then passes through the object on the stage, and then reaches the 2D X-ray detector. Note that typically, the X-ray absorption capability of the filter element is constant in the direction of the rotation axis (x).

In a preferred embodiment of the inventive CT apparatus, the filter element is made of a material exhibiting a higher absorption for low energy X-rays than for high energy X-rays. By this means, the energy spectrum of the X-ray source is modulated; the fraction of high energy X-rays increases as compared to low energy X-rays. Low energy X-rays are more absorbed in human or animal tissue than high energy X-rays, and therefore tend towards causing more accumulated damage to body tissue and/or DNA. High energy X-rays, in contrast, are well suited for transmission through relatively thick body parts, such as the head or the chest, yielding good contrast still.

In a preferred further development of the above embodiment, the material exhibits an absorption coefficient $\mu$ for 5 keV X-rays which is at least 10 times larger, preferably at least 50 times larger, than an absorption coefficient $\mu$ for 40 keV X-rays. This reduces damage to the object and at the same time provides good depth contrast. Note that the absorption behavior of a material can be adjusted in particular via the atomic number of elements contained. Note that the material of the filter element can also be chosen with $\mu$ (5 keV) being at least 20 times larger, and preferably at least 100 times larger, than $\mu$ (40 keV), in accordance with the invention.

In another preferred embodiment, the filter element is made of aluminum or a material containing aluminum. Aluminum (Al) exhibits an absorption strongly dependent on the X-ray energy. Preferably, the material contains at least 30 wt % (percent per weight) of Al, more preferably at least 50 wt % of Al, and most preferably at least 80 wt % of Al.

Particularly preferred is an embodiment wherein the filter element has a spatially varying thickness along the cross direction (y), with a maximum thickness at the zero position (y0). This is the simplest way to establish a spatially varying X-ray energy distribution and absorption capability of the filter element, typically with the material of the filter element having a homogeneous (spatially constant) absorption coefficient. The thickness is measured in parallel to the beam axis (z). Note that typically, the thickness does not vary along the direction of the rotation axis (x). Further note that alternatively or in addition, the density and/or the composition of the material of the filter element may vary along the cross direction (y) in order to establish a varying X-ray absorption capability.

In a further development of this embodiment, the filter element exhibits a thickness variation along the cross direction (y) by a factor of 2 or more, preferably by a factor of 5 or more, in the area of the filter element which shadows the detection area of the 2D x-ray detector. Such a variation can easily be manufactured and establishes an intensity variation of the transmitted high energy X-rays at the projection images which can well be compensated for under typical measurement conditions. Note that thickness variation typically does not exceed a factor of 20, though.

In an advantageous embodiment, the spatially varying X-ray absorption capability exhibits an absorption variation along the cross direction (y) by a factor of 5 or more, preferably by a factor of 20 or more, most preferably by a factor of 50 or more, in the area of the filter element which shadows the detection area of the 2D X-ray detector. The factors apply at least to X-rays of 5 keV (and preferably to all low energy X-rays of about 1 keV-10 keV), and possibly also to high energy X-rays (with an X-ray energy of about 10 keV-100 keV); however note that the absolute absorption is typically much less for high energy X-rays than for low energy X-rays. The factors compare the strongest filtered X-ray intensity with the weakest filtered X-ray intensity behind the filter element (assuming a uniform illumination of the filter element). This embodiment has shown good radiation dose reduction and still high image quality in practice. An intensity factor of about 50 (and often more) for the projection images can, under typical measurement conditions, still be compensated for by back projection when calculating cross-sections.

Also preferred is a an embodiment wherein the X-ray absorption capability exhibits a monotonic decreasing absorption, in particular strict monotonic decreasing absorption, on both sides away from the zero position (y0) along the cross direction (y), in the area of the filter element which shadows the detection area of the 2D X-ray detector. With increasing distance from the rotation axis, the information from the entirety of the projection images becomes less, and therefore less absorption of the filter element can be compensated for. With this embodiment, gradually more X-ray intensity is provided at the object when departing from the rotation axis, so uniform cross-section image quality may be obtained in summary. With a strict monotonic decreasing absorption, sharp changes in the absorption capability of the filter element are excluded, so artefacts in image reconstruction are avoided. Note that this embodiment is typically realized by a thickness variation of the filter element exhibiting a monotonic decreasing thickness, in particular strict monotonic decreasing thickness, on both sides away from the zero position (y0) along the cross direction (y), in the area of the filter element which shadows the detection area of the 2D X-ray detector.

Another preferred embodiment provides that the spatially varying X-ray absorption capability exhibits at least approximately a Gaussian type distribution of the absorption with respect to the cross direction (y), centered around the zero position (y0), in the area of the filter element which shadows the detection area of the 2D X-ray detector. With the Gaussian type distribution, the intensity reduction towards the rotation axis approximately matches the information increase such that a uniform image quality within a cross-section (from its center to its edges) is obtained. The absorption capability is considered to be approximately of Gaussian type if the actual absorption deviates from an exact Gaussian distribution by at most 10% (with the basis being the exact Gaussian distribution), in the area of the filter element which shadows the detection area of the 2D X-ray detector. Note that equally preferred is a thickness variation of the filter element exhibiting at least approximately a Gaussian type distribution of the thickness with respect to the cross direction (y), centered around the zero position (y0), in the area of the filter element which shadows the detection area of the 2D X-ray detector. The thickness variation is considered to be approximately of Gaussian type if the actual thickness deviates from an exact Gaussian distribution by at most 10% (with the basis being the exact Gaussian distribution), in the area of the filter element which shadows the detection area of the 2D X-ray detector. Again, a basically uniform image quality within a cross-section (from its center to its edges) may be obtained.

Further preferred is an embodiment wherein the X-ray source is a microfocus X-ray tube, in particular with a tungsten anode. By this means, a high intensity of polychromatic radiation with high energy X-rays of up to about 65 keV, or even up to about 100 keV, may be obtained.

In another preferred embodiment, an object to be investigated is located on the stage, in particular with longitudinal object orientation along the rotation axis (x). By this means, the object can be investigated with a minimum radiation dose. The object may be located such that parts (e.g. organs of a live human or animal) particularly sensitive to radiation damage are intersected by the rotation axis or located close to the rotation axis. Further, the object may be scanned easily by translation along the direction of the rotation axis by means of the longitudinal object orientation.

In a highly advantageous embodiment, the stage is moveable along a longitudinal axis (LA) which is parallel to the rotation axis (x). By this means, larger volumes of the object may be investigated by scanning along the longitudinal axis. Note that the translation along the longitudinal axis is typically motor driven and automated.

Also within the scope of the present invention is the use of an inventive CT apparatus described above, characterized in
that an object to be investigated is located on the stage,
that a plurality of projection images of the object are recorded with the 2D X-ray detector at different rotation positions of the gantry system,
and that from the dataset of projection images, a dataset of cross-sections is generated by a back projection reconstruction algorithm. By this means, good quality 3D images of the object may be obtained at a reduced radiation dose for the object, in particular a living object. The back projection (in particular filtered back projection) reconstruction algorithm compensates for the signal to noise reduction due to reduced intensity in the center region near the rotation axis. The closer a volume pixel is to the rotation axis, the more projection images contain information from this volume pixel which is available for compensation purposes.

Particularly preferred is a variant of the inventive use, in correlation with the inventive CT apparatus comprising a movable stage, wherein the plurality of projection images of the object are recorded also at different movement positions of the stage along the longitudinal axis (LA). By this means, a volume of the object extending arbitrarily far along the longitudinal direction may be investigated.

Further preferred is a variant of the inventive use wherein the object is a living animal of up to the size of a rat or a non-living object of up to the same size. With objects of a relatively small size, such as up to a rat (comparable to a cylindrical volume of about 8 cm in diameter and 20 cm in length), a relatively large fraction of the object can benefit from the higher information density close to the rotation axis, so the achievable radiation reduction is particularly significant here. However note that the invention can also be used for CT apparatus dimensioned for scanning complete human beings.

Further advantages can be extracted from the description and the enclosed drawing. The features mentioned above and below can be used in accordance with the invention either individually or collectively in any combination. The embodiments mentioned are not to be understood as exhaustive enumeration, rather have exemplary character for the description of the invention.

The invention is shown in the drawing.

DESCRIPTION OF THE PREFERRED EMBODIMENT

In X-ray computed tomography, a large number of X-ray images (projection images) are recorded, with each recording coming along with an exposure of the object to be investigated with X-rays. X-rays may damage the material exposed, in particular by ionization. In human or animal tissue, X-rays may in particular induce carcinogenesis. The present invention therefore seeks to reduce the radiation dose to objects investigated in X-ray computed tomography.

The absorbed dose depends on absorbing coefficients of materials in the object, thickness of the object materials, and the intensity and energy distribution in the primary beam. The first two factors cannot be changed by the scanning setup, but the energy spectrum and intensity distribution in the primary beam can be adjusted in such a way that the absorbed dose will be reduced without significant impact to the quality of results of tomographical reconstruction, in accordance with the invention.

The central, in general thickest part of the object to be investigated, such as an animal or human body, absorbs much more radiation than peripheral parts with shorter passages of the X-ray beam through the body. At the same time, the central part of the body contains organs most sensitive to radiation damages.

The invention is based on the idea of a spatial modulation of the energy spectrum and the intensity of the primary beam by such a way that the central part of the body will receive less intensity and higher energy of X-ray radiation. Both intensity reduction and spectral shift to higher energies are reducing dose rate absorbed by this most sensitive part of the body. Such a reduction of intensity in the primary beam may reduce the signal on the central part of the detector array behind the object, which in general will at least partially, and in most cases practically completely be compensated during tomographical reconstruction, since the central part of the reconstructed area is covered by a more-consistence ray pattern during the back-projection procedure.

Figure 1:
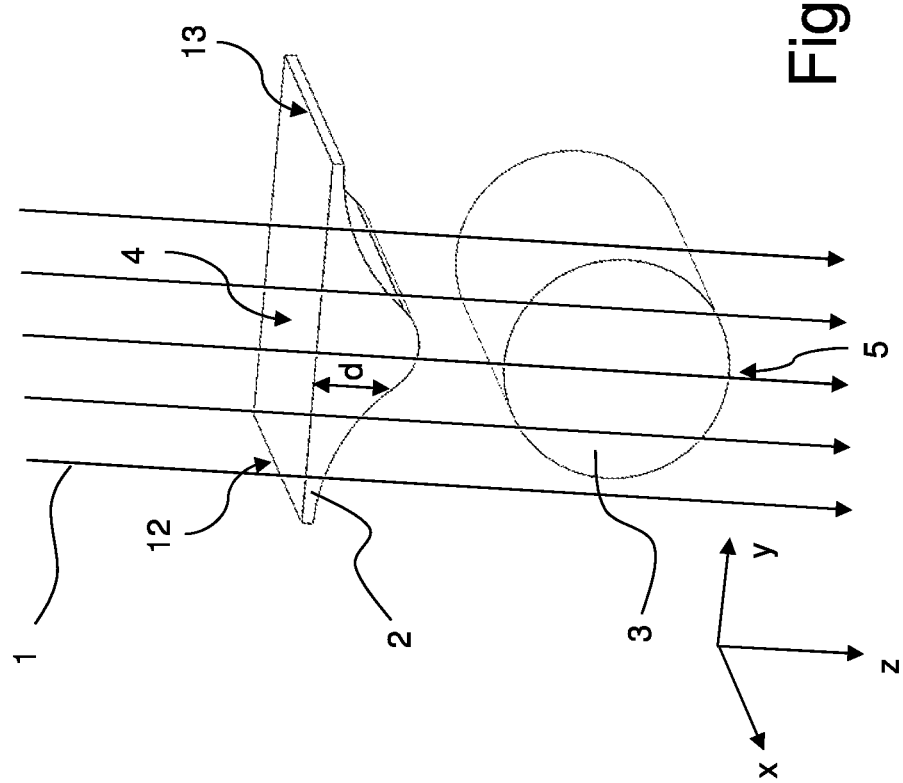
FIG. 1 shows a schematic view of the arrangement of a filter element in an X-ray beam in front of an object to be investigated, for the invention.

The core of the present invention is a beam-shaping filter element, an embodiment of which is shown in FIG. 1. FIG. 1 shows a primary X-ray beam 1 (here of parallel type), directed onto a beam-shaping filter element 2. The filter element 2 shadows an object 3 to be investigated, i.e. the X-ray beam 1 is attenuated (but not completely blocked) when passing through the filter element 2. The filter element 2 has a variable local thickness d (measured z direction, along which the X-ray beam 1 propagates), with its maximum thickness at its center 4, which is aligned here with the center 5 of the object 3, both with respect to the y direction. The thickness d decreases symmetrically towards the sides, and minimum thicknesses are reached at the edges 12, 13.

The size (width) of the beam-shaping filter element 2, both in x and y direction, is similar to the size of the object 3 in the case that the filter element 2 is placed close to the object and far from the X-ray source (not shown); this situation is illustrated in FIG. 1. In the case of a short distance between such a beam shaping filter element 2 and an emission point inside the X-ray source, the size of the filter element 2 should be reduced proportionally. Note that it is generally preferred that no unfiltered X-rays reach the detector; if necessary, a too small filter element may be complemented with an aperture to match the x-ray beam cross-section. The selection of the filter material is dependent on the energy distribution of emission from the X-ray source. For the most typical range of energies between 40 and 100 keV for in-vivo microtomography of small laboratory animals, the material can be Al or Al alloys. The peak thickness and the thickness distribution of the filter element 2 across the beam (in y direction) is chosen such that a significant cut of the low-energy part of X-ray spectrum in the central part of the beam is achieved, while keeping enough intensity of the primary beam in this part for obtaining a reasonable signal-to-noise ratio on the detector behind the object. With the object in place, the cut (attenuation) in the low-energy part of X-ray spectrum in the central part of the object does not significantly change the signal distribution (with respect to both intensity end energy) arriving at the detector, because the object in the central part is also working as a strong filter for low energy radiation. The absorption of the low-energy photons by the beam-shaping filter element 2 before they reach the object makes a big improvement (i.e. reduction) in the dose absorbed inside the body, though, especially in the parts facing towards primary beam. The shape of the filter element surface should be smooth enough to avoid sharp intensity and spectrum variations, which can create reconstruction artifacts.

In a practical implementation of such a beam-shaping filter element in accordance with the invention, for an in-vivo small animal microtomography system, Al was used as a filter material with thickness variation from 0.5-0.8 mm in the side parts of the filter element up to 5-6 mm in the central part. The polychromatic radiation from a microfocus X-ray tube with peak energy up to 65 keV and a Tungsten anode was used as a primary beam. A measured value of the dose rate, absorbed by an animal, has been estimated using a rate meter with a probe surrounded by a "mouse-size" plastic phantom. Using the described above beam-shaping filter element allows reducing the absorption dose 2-5 times compared to scanning with standard flat Al filters 0.5-1 mm thick and scanning with a non-filtered primary beam. Such reduction of the absorbed dose produces only very small influence on the quality of results, obtained after tomographical reconstruction.

Figure 2:
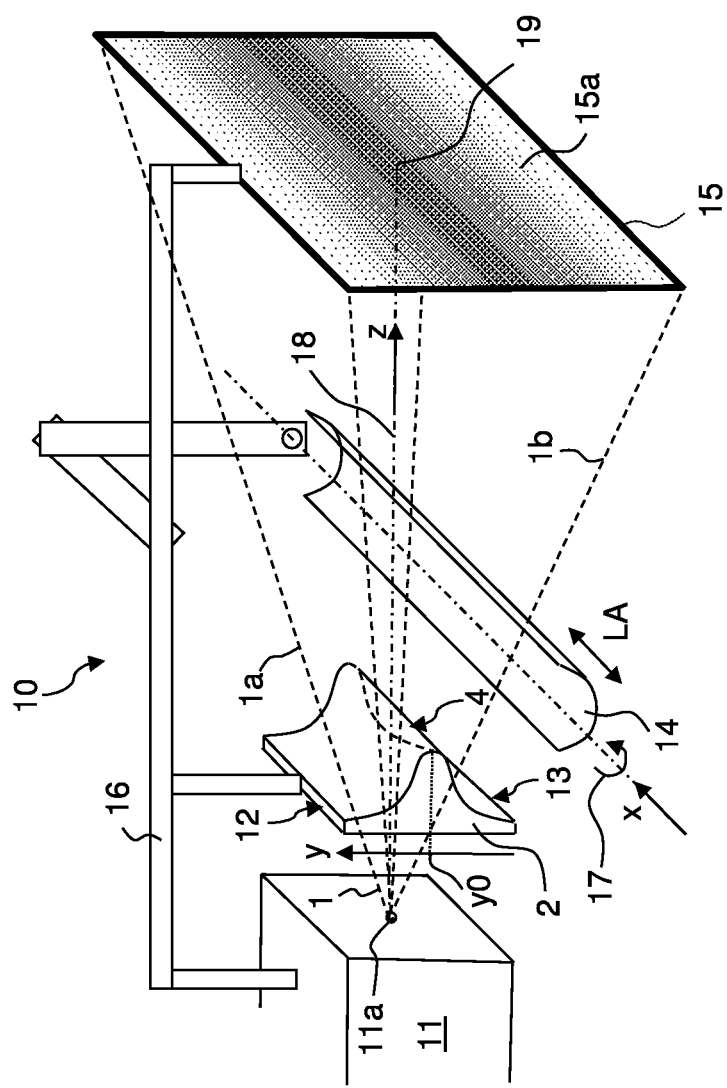
FIG. 2 shows a schematic view of an embodiment of an inventive CT apparatus.

FIG. 2 shows an embodiment of an X-ray CT apparatus 10 in accordance with the invention.

An X-ray source 11 emits at an X-ray beam 1, here of divergent type, along a (central) beam axis z. The X-ray beam 1 then reaches a filter element 2 made of aluminum here, where the X-ray beam 1 is attenuated as a function of the location in a cross direction y, which extends perpendicular to the beam axis z. At a center 4, i.e. at a zero position y0 in y direction, the thickness (measured in z) of the filter element 2 is maximum, and towards both sides (in FIG. 2 up and down) or edges 12, 13, respectively, the thickness decreases in a strict monotonic way. The thickness in z as a function of y is approximately of Gaussian type here, centered around y0. In a longitudinal direction which is perpendicular to both z and y, compare x, the thickness of the filter element 2 is not changing (note that in case of an uneven intensity distribution in x direction of the X-ray source 11, or in the X-ray beam 1, respectively, the thickness of the filter element 2 may be varied in x direction correspondingly, though). The shape of the filter element 2 leads to a strong attenuation of the X-ray beam 1, in particular for its low energy part, near the center 4, and to a decreasing attenuation towards the edges 12, 13. Since the thickness at the center is here about 5 times larger than the thickness at the edges 12, 13, the variation of absorption should be at least about a factor of 5, and typically is much higher due to the exponential absorption behavior.

The attenuated X-ray beam 1a then approaches a stage 14, here designed as a bed for a living animal of up to the size of a rat as an object (not shown) to be investigated. Close to the stage 14, in an area where the object is to be placed, lies a rotation axis x of the CT apparatus 10. The rotation axis x runs perpendicular to both the beam direction z and the cross direction y. The part of the X-ray beam 1 which passes the filter element 2 at the center 4 runs through the rotation axis x; in other words, the emission point 11a of the X-ray source 11, the center (or rather center line) 4 and the rotation axis x lie in the same plane.

The X-ray beam 1b after passing the stage 14 (and the object not shown) finally reaches a 2D X-ray detector 15 (also called camera) for recording projection images of the object. If no object is on the stage 14, the X-ray intensity distribution on the detection area 15a will exhibit a minimum level (marked dark) in a central plane corresponding to the zero position y0 at the center 4 of the filter element 2 or the rotation axis x, respectively, and increasing levels (marked lighter) when going up or down, with respect to the y direction. Accordingly, when placing an object at the stage 14, parts of the object intersected by the rotation axis x exhibit a minimum radiation dose, and the radiation dose increases with larger distance from the rotation axis x in y direction. More specifically, central part X-rays 18 of the X-ray source 11 propagating along the beam axis z (or in the corresponding xz plane) pass the filter element 2 at zero position y0 in y direction, intersect the rotation axis x and reach the detection area 15a here at its center 19, wherein said center part X-rays 18 experience a maximum absorption at the filter element 2. In contrast, X-rays with a higher or lower y position at the filter element 2 as compared to y0 will experience less absorption at the filter element 2. It should be noted that preferably, the filter element 2 shadows the complete detection area 15a of the 2D X-ray detector 15.

For obtaining projection images from different angles with respect to the object, a gantry system 16 is provided. In the embodiment shown, the gantry system 16 couples the X-ray source 11, the filter element 2 and the 2D X-ray detector 15 and allows the rotation of the entirety of said items with respect to the rotation axis x, i.e. around the non-rotating stage 14, compare rotation arrow 17. Note that it is also possible to have a gantry system 16 which rotates the stage 14 relative to the fixed entirety of the X-ray source 11, the filter element 2 and the 2D X-ray detector 15, in accordance with the invention. The stage 14 is further movable along a longitudinal axis LA (which is in parallel with the rotation axis x), so projection images can be obtained for different rotation positions of the gantry system 16 and for different translation positions along the longitudinal axis LA of the stage 14.

In summary, the invention presents a particular design of the filter element 2 which is placed in between the X-ray source 10 and the object on the stage 14 of a CT apparatus 10. As the X-rays 1 are attenuated by the filter element 2, the 3D shape of the filter element 2 will result in an uneven distribution in such a way that the center 4 of the filter element 2 along the cross direction y attenuates and cuts out low X-ray energies more as compared to the peripheral part. The 3D shape of the filter element 2 is to maximize the attenuation of the X-rays in the center 4 along the Y-axis. As X-rays pass through the filter element 2, there is an exponential decay in the X-rays that reach the camera the closer to the center 4 the X-rays pass through the filter element 2, where it has the maximum thickness (along the Y-axis). This is based on the Beer-Lambert law: $I=I_0 e^{-\mu d}$ where d is the thickness of the material, $\mu$ is the absorption coefficient of the material, I is the transmitted intensity and $I_0$ is the initial intensity. Because of the exponential decrease in X-rays reaching the camera in the central position (along the Y-axis) the result is a decrease in the radiation dose. This uneven distribution also results in a reduced signal to noise ratio in the center of the camera on the projection images, but is overcome by the reconstruction algorithm (back projection) when calculating the cross-sections. This is based on the fact that during the back projection there is more information as you reconstruct closer to center of the rotation axis (comparable to the distance between the spokes on wheel, where the closer you get to the center, the smaller the distance becomes). The combination of the 3D shape of the filter and the back projection algorithm used results in a reduced radiation dose without compromising the image quality.

We claim:

1. An X-ray computed tomography (=CT) apparatus, the apparatus comprising:
    an X-ray source emitting an X-ray beam or a divergent X-ray beam, along a beam axis;
    a stage for an object to be investigated with an attenuated X-ray beam;
    a filter element disposed between said X-ray source and said stage and attenuating said X-ray beam, said filter element having a spatially varying X-ray absorption capability along a cross direction which is perpendicular to both said beam axis and to a rotation axis, said spatially varying X-ray absorption capability exhibiting a maximum absorption along said cross direction at a zero position, wherein X-rays passing through said filter element at said zero position intersect said rotation axis;
    a 2D X-ray detector disposed downstream of said stage, said 2D X-ray detector having a detection area; and
    a gantry system structured to simultaneously rotate an entirety of said X-ray source, said filter element and said 2D X-ray detector about said rotation axis or structured to rotate said stage for the object about said rotation axis, wherein said rotation axis is perpendicular to said beam axis.

2. The CT apparatus of claim 1, wherein said filter element is made of a material exhibiting a higher absorption for low energy X-rays than for high energy X-rays.

3. The CT apparatus of claim 2, wherein said material exhibits an absorption coefficient for 5 keV X-rays which is at least 10 times larger or at least 50 times larger than an absorption coefficient for 40 keV X-rays.

4. The CT apparatus of claim 1, wherein said filter element is made of aluminum or of a material containing aluminum.

5. The CT apparatus of claim 1, wherein said filter element
    has a spatially varying thickness along said cross direction, with a maximum thickness at said zero position.

6. The CT apparatus of claim 5, wherein said filter element exhibits a thickness variation along said cross direction by a factor of 2 or more or by a factor of 5 or more, in an area of said filter element which shadows said detection area of said 2D X-ray detector.

7. The CT apparatus of claim 1, wherein said spatially varying X-ray absorption capability exhibits an absorption variation along said cross direction by a factor of 5 or more, a factor of 20 or more or a factor of 50 or more, in an area of said filter element which shadows said detection area of said 2D X-ray detector.

8. The CT apparatus of claim 1, wherein said X-ray absorption capability exhibits a monotonic decreasing absorption or a strict monotonic decreasing absorption, on both sides away from said zero position along said cross direction, in an area of said filter element which shadows said detection area of said 2D X-ray detector.

9. The CT apparatus of claim 1, wherein said spatially varying X-ray absorption capability exhibits at least approximately a Gaussian type distribution of absorption with respect to said cross direction, centered around said zero position, in an area of said filter element which shadows said detection area of said 2D X-ray detector.

10. The CT apparatus of claim 1, wherein said the X-ray source is a microfocus X-ray tube.

11. The CT apparatus of claim 10, wherein said the X-ray source has a tungsten anode.

12. The CT apparatus of claim 1, wherein the object to be investigated is located on said stage.

13. The CT apparatus of claim 12, wherein a longitudinal object orientation is along said rotation axis.

14. The CT apparatus of claim 1, wherein said stage is moveable along a longitudinal axis which is parallel to said rotation axis.

15. A method for using the CT apparatus of claim 1, wherein an object to be investigated is located on the stage and a plurality of projection images of the object are recorded with the 2D X-ray detector at different rotation positions of the gantry system and a dataset of cross-sections is generated by a back projection reconstruction algorithm from a dataset of projection images.

16. The method of claim 15, wherein a plurality of projection images of the object are also recorded at different movement positions of said stage along a longitudinal axis which is parallel to said rotation axis.

17. The method of claim 15, wherein object is a living animal of up to a size of a rat or a non-living object of up to that size.

* * * * *